(12) United States Patent
Illyes et al.

(10) Patent No.: US 7,468,037 B2
(45) Date of Patent: Dec. 23, 2008

(54) APPARATUS AND METHOD FOR MEASURING HEMODYNAMIC PARAMETERS

(76) Inventors: Miklos Illyes, No. 163 Street Ketujfalu, H-1182 Budapest (HU); Jozsef Beres, No. 73 Street Rakoczi, H-2217 Gomba (HU)

( * ) Notice: Subject to any disclaimer, the term of this patent is extended or adjusted under 35 U.S.C. 154(b) by 73 days.

(21) Appl. No.: 10/596,240

(22) PCT Filed: Feb. 16, 2005

(86) PCT No.: PCT/HU2005/000012

§ 371 (c)(1),
(2), (4) Date: Jun. 5, 2006

(87) PCT Pub. No.: WO2005/007265

PCT Pub. Date: Aug. 25, 2005

(65) Prior Publication Data

US 2007/0106162 A1     May 10, 2007

(30) Foreign Application Priority Data

Feb. 18, 2004   (HU)   .................................. 0400426
Feb. 3, 2005    (HU)   .................................. 0500169

(51) Int. Cl.
*A61B 5/02* (2006.01)
(52) U.S. Cl. ........................ 600/490; 600/300
(58) Field of Classification Search ................ 600/490, 600/300, 494, 495, 504
See application file for complete search history.

(56) References Cited

U.S. PATENT DOCUMENTS

| | | | | |
|---|---|---|---|---|
| 5,054,493 A | * | 10/1991 | Cohn et al. | 600/485 |
| 5,238,001 A | * | 8/1993 | Gallant et al. | 600/513 |
| 5,241,966 A | * | 9/1993 | Finkelstein et al. | 600/485 |
| 5,265,011 A | * | 11/1993 | O'Rourke | 600/485 |
| 5,680,870 A | | 10/1997 | Hood, Jr. et al. | |
| 6,117,087 A | | 9/2000 | Kamm et al. | |
| 6,258,035 B1 | * | 7/2001 | Hoeksel et al. | 600/481 |

(Continued)

FOREIGN PATENT DOCUMENTS

EP   1 264 573   12/2002

(Continued)

OTHER PUBLICATIONS

Davies, Justina Ina et al. "Pulse wave analysis and pulse wave velocity: a critical review of their strengths and weaknesses." Journal of Hypertension 2003, vol. 21, No. 3, pp. 463-472.

(Continued)

*Primary Examiner*—Charles A Marmor, II
*Assistant Examiner*—Anita Saidi
(74) *Attorney, Agent, or Firm*—Collard & Roe, P.C.

(57) ABSTRACT

An apparatus for measuring hydrodynamic parameters, especially for Augmentation Index (Aix) and/or Ejection Duration (ED), by non-invasive, cuff based occlusive, blood pressure measurement, which apparatus comprises occlusive, oscillometric automatic blood pressure meter and units. There can also be a method for non-invasive measurement of hemodynamic characteristics, especially AN and/or ED with an occlusive, pressure sensor cuff, placed on the brachial artery, wherein the apparatus according to the invention samples and analyzes and evaluates the signal flow of the oscillations of pulse waves using an unusual stepwise blood pressure measurement.

11 Claims, 6 Drawing Sheets

U.S. PATENT DOCUMENTS

| | | | |
|---|---|---|---|
| 6,398,727 B1 * | 6/2002 | Bui et al. | 600/300 |
| 6,702,754 B2 * | 3/2004 | Ogura et al. | 600/500 |
| 6,712,768 B2 | 3/2004 | Ogura et al. | |
| 6,994,675 B2 * | 2/2006 | Sharrock | 600/500 |
| 7,029,449 B2 * | 4/2006 | Ogura | 600/500 |
| 7,326,180 B2 * | 2/2008 | Tanabe et al. | 600/500 |
| 2003/0135094 A1 | 7/2003 | Illyes et al. | |

FOREIGN PATENT DOCUMENTS

| | | |
|---|---|---|
| EP | 1 332 715 | 8/2003 |
| EP | 1 340 453 | 9/2003 |
| HU | 220 528 B1 | 11/1999 |
| HU | 222 052 B1 | 6/2000 |
| WO | WO 90/11043 | 10/1990 |
| WO | WO 01/37727 | 5/2001 |

OTHER PUBLICATIONS

Wilkinson, Ian B. et al. "Heart Rate Dependency of Pulse Pressure Amplification and Arterial Stiffness." American Journal of Hypertension, Jan. 2002: vol. 15, No. 1, Part 1, pp. 24-30.

* cited by examiner

APPARATUS AND METHOD FOR MEASURING HEMODYNAMIC PARAMETERS

CROSS REFERENCE TO RELATED APPLICATIONS

Applicants claim priority under 35 U.S.C. §119 of Hungarian Application No. P0400426 filed on Feb. 18, 2004 and Hungarian Application No. P0500169 filed on Feb. 3, 2005. Applicants also claim priority under 35 U.S.C. §365 of PCT/HU2005/000012 filed on Feb. 16, 2005 the disclosures of all of these applications are hereby incorporated herein by reference.

BACKGROND OF THE INVENTION

1. Field of the Invention

The subject matter of the invention is an apparatus for measurement of characteristic data of hemodynamics, furthermore for complex examination of the cardiovascular system by oscillometric (occlusive) measurement using cuff. The apparatus comprises oscillometric automatic blood pressure meter and completing units. Another subject matter of the invention is a method for measurement.

2. Description of Related Art

There is a close relation between hypertension and development of arteriosclerosis. The most spread method from among others is the measurements of the aorta (main artery) augmentation index (AIx) and the Pulse Wave Velocity, i.e. the artery stiffness measurement. The PWV gives information about the elasticity of the aorta wall. In addition to the elasticity of aorta wall the AIx gives information also about the resistance of the peripheral arteries and the vascular tonus. The AIx is the difference between the amplitude of first systolic wave produced by the heart contraction and the second one produced by the reflection of the first wave in percents of the greater one. In the measuring of the PWV the time difference between the arrivals of pulse wave to the jugular artery and the femoral one, the distance between the two points of measurement are defined and the velocity of pulse wave on the aorta is calculated. There is a recent endeavour to solve this task by a non-invasive method instead of catheter inserted into the aorta root. Such solutions are described in the U.S. Pat. No. 6,117,087 and in the international application WO 90/11043. The pulse curves recorded in them are however not completely conform to those of the aorta so the central pulse curve is reconstructed by a mathematical method from the peripheral one. A transformation model is developed for this purpose using results of a number of invasive measurements and non-invasive ones, as well as e. g. Fourier-series. The measurement performed on the upper arm i. e. on the arteria brachialis or on the arteria radialis e. g. on the wrist does not provide, however, sufficient information about the processes of arteriosclerosis in the arteries, primarily in the central elastic ones. (Davies, J. I. and colleague: Pulse wave analysis and pulse wave velocity: a critical review of their strengths and weaknesses. *J. Hypertens,* 2003, Vol. 21 No. 3. 463-472.). It should also be taken into account that the examinations performed with contact pressure sensors are inevitably inaccurate due to the inevitable movements of both the examining person and the examined one during the examination.

The measuring apparatuses Sphygmocor (Atcor) and Complior (Artech Medical) using also contact pressure sensors allow non-invasive measurement of PWV. Arterial pulse is sensed on two points of the patient's body surface, on the jugular artery (arteria carotis) and on the femoral one (arteria femoralis) and the time points of appearance of pulse are measured on the two arteries. The pulse wave velocity is defined from the time difference between the pulse on the two points and the distance between them.

The greatest deficiency of the above-mentioned methods is that their application is difficult, requiring experienced specialists and takes too long time, as well. The patient cannot use it independently in his or hers home and he or she cannot operate alone the apparatus. In addition the apparatus is extraordinarily expensive. The U.S. Pat. No. 6,712,768 patent seeks to eliminate these deficiencies, wherein the pulse wave curves received from the blood pressure measuring cuff on the upper arm are examined to measure Aix. The time between the appearance of the first wave generated by the heart contraction and that of the second wave generated by the reflection of the primary one from the lower part of body, which is defined using a pressure curve obtained by a cuff inflated above the systolic pressure, then these points of time are measured on the curve measured in the range under diastolic pressure and AIx is defined using the amplitudes obtained in this way. The details of the pulse wave between the diastolic value and the MAP (=Mean Arterial Pressure), which is the point of highest amplitude on the parabolic pressure curve of the traditional stepwise performed blood pressure measurement, cannot be reliably measured, because the shape of the pulse curve may significantly change even at small pressure change in the cuff. The cuff gets looser and looser in the pressure range under diastole, the tension of vessel wall increases, consequently the amplitude of oscillation, as well as the recordable signal significantly decreases. In consequence of these causes AIx cannot be defined so accurately as it is required for medical or clinical practice.

The ED (=ejection duration) i. e. the time of open state of aortic valve is a hemodynamic characteristic having similar importance as the previously mentioned ones. During one heart cycle a certain point of the wave trough, within a cardiac cycle, is denoted as the end of time point of blood ejection of the left chamber. (Wilkinson, I. B. and colleagues: Heart Rate Dependency of Pulse Pressure Amplification and Arterial Stiffness. *Am. J. Hypertens.* 2002; 15:24-30.) The known non-invasive methods are, however, not suitable to separate reliably the reflex waves, and to determine the end-point of ED. The AIx and ED values thus cannot be determined by these known methods with accuracy and reliability equal to those of invasive examinations.

SUMMARY OF THE INVENTION

The purpose of the present invention is to develop a simple and relatively inexpensive non-invasive examining apparatus for measuring such hemodynamic characteristics, as Augmentation Index (AIx), Ejection Duration (ED) and Pulse Wave Velocity (PWV) etc., as well as for complex examination of the cardiovascular system.

Another purpose of the invention is that the measuring apparatus could be used as professional physician's apparatus, but the patient himself or herself should be also able to perform alone the measurement with it and the apparatus should be applicable for usage in a "home care" system or to be combined with a portable ambulatory blood pressure measuring monitor for 24 hours' usage (ABPM) or an ABPM with ECG unit.

The invention is based on the recognition that the task may be accomplished within the framework of the well-known and generally used oscillometric blood pressure measurement with cuff (occlusively), if the automatic blood pressure meters are provided with units for processing and evaluation of oscillation wave.

We found that if the sampling density is at least twice and the signal recording density are at least four times higher than those of the traditional measurement the hemodynamic characteristics become recognisable and suitable for processing.

We found also, that the analysis of the heart-cycle oscillation curve with the required high resolution is possible only with a device able to compensate ("anti-filtering") the unavoidable distortions arising at the decomposition of the analogue input sign to AC and DC components by a RC unit, using the exact inverse function of the transmission frequency characteristic of the RC unit for the compensation. Accordingly we may include a compensating (anti-filtering) unit into the device, which provides elimination of the noise and distortion from the digitised signal series of the oscillation curve.

Our above mentioned recognitions give the possibility for detailed analysis of the oscillation curves (oscillation pulse) received at oscillational blood-pressure measurement, which lead to further recognitions. We found the astonishing recognition on the base of the large oscillometric database created during our biological research that the oscillation curve detected by ordinary oscillation blood pressure measurement on the arteria brachialis has identical main characteristics with the pressure pulses and the artery diameter pulses from the viewpoint of practice and clinical praxis. This fact is proved by the concordance of the places marked as "primary wave" and "secondary wave" of the curves. We found also astonished out that the time between the beginning of the heart cycle and that of appearance of the second reflection measured on the oscillation curve of pulse wave measured by cuff is exactly four times longer than the conveyance time between the arteria carotis and arteria femoralis measured by direct method. This fact confirms that we measure the pressure wave of central aorta during our examinations, and we observe indeed the reflex-waves arriving immediately from the central aorta. The results are in concordance with the results measured simultaneously by the above-mentioned Complior device within the error limit. We examine the elasticity of the central aorta with this measurement. It may be verified using the known Valsalva-effect. When the muscles of abdomen and chest are strained the expansiveness of the aorta increases and the conveyance speed of the pulse wave decreases. The information obtained in this way is correct as our examinations attest if the measurement is performed at the appropriate pressure in the cuff. A change of even 10 millimetres of mercury causes significant change in the oscillogram and leads to false results. This is the reason why the measurement of the hemodynamical characteristics should be performed at the cuff pressure defined by a previous traditional blood pressure measurement. The locations and amplitudes of the main wave and the first reflected one should be measured at a supra-systolic pressure completely closing the artery, optimally at a cuff pressure of 35 millimetres of mercury above the systolic one. The measurement at free blood flow should be performed at the measured diastolic pressure. The usage of a pressure either within the interval between diastolic pressure and MAP (mean arterial pressure) or the pressure under diastole does not provide correct result.

The summarized essence of our recognition underlying the invention is that if the pulse curves obtained in the oscillation blood pressure measurement are recorded with a resolution higher than the usual one not only their highest amplitudes as in the currently used blood pressure meter but the whole oscillation curve together with the induced reflected waves may be used for the evaluation. The AIX, PWV, and ED may be defined with a blood pressure meter with cuff in non-invasive way, with a measurement in one point instead of the complicated measurement of two points. Even the patient himself or herself can perform the examination and the apparatus may be simply incorporated in a "home care" system. Professional variants may also be developed for physician's or medical researchers' usage.

The solution according to invention based on the above discussed recognition is an apparatus for measuring hemodynamic parameters, especially Augmentation Index (AIx) and/or Ejection Duration (ED), by non-invasive, cuff based, occlusive, blood pressure measurement, which apparatus comprises occlusive, oscillometric automatic blood pressure meter and units, determining the values of hemodynamic parameters. The apparatus according to our invention may be characterised by that the apparatus has an oscillation wave separating and storing signal detector, the sampling rate thereof is at least 200/heart cycle; and has a storage unit having organisation of at least 9 bits; a preferably digital anti-filter to compensate the distortions rising at the sampling, separating and digitising of the oscillation wave; an amplitude arithmetic unit establishing the Augmentation Index (AIx); and a synthesising unit, which establishes the Ejection Duration (ED).

The apparatus according to our invention may be advantageously characterised by that the sampling rate of the signal detector is 180 to 220/second.

The apparatus according to our invention may be also advantageously characterised by that the storage unit storing the signals generated by the oscillation wave has organisation of 10 to 12 bits.

The apparatus according to our invention may be yet advantageously characterised by that it is equipped with a time-arithmetic unit establishing the Pulse Wave Velocity (PWV), and/or integrator unit establishing the Systole Area Index (SAI) and Diastole Area Index (DAI).

The apparatus according to our invention may be advantageously characterised furthermore by that the amplitude arithmetic, the time-arithmetic in a concrete case, and the integrator unit are connected to a common program controller, and included into a common analyser.

An advantageous embodiment of the apparatus according to our invention may be characterised by that it is combined with a portable 24 h ambulatory blood pressure monitor. Another advantageous embodiment of the apparatus according to our invention may be characterised by that it is incorporated in a telemedical home care system.

Finally an advantageous embodiment of the apparatus according to our invention may be characterised by that it is combined with a 24 h blood pressure monitor built together with an ECG and controlled by it.

Another subject-matter of the invention is a method for non-invasive measurement of hemodynamic characteristics, especially Augmentation Index (AIx) and/or Ejection Duration (ED), with an occlusive, pressure-sensor cuff, placed on the brachial artery, and with the above-mentioned apparatus, by sampling, analysing, and evaluation of the signal flow of the oscillations of the pulse waves. The method according to our invention may be characterised by that a usual stepwise blood pressure measurement is performed, and the SBP, DBP and HR values are stored, thereafter the signal distortions arisen at the sampling are compensated by an "anti-filtering" process, after it the cuff is set over the systolic pressure, i.e. to supra-systolic pressure range, preferably to SBP+35 millimetres of mercury, and the Augmentation Index (AIx) is calculated from the received oscillation curves on the basis of the wave amplitudes, and the Ejection Duration (ED) value is established by determining the minimum-point after the first reflex wave on the oscillation curve.

The method according to invention may be advantageously characterised by that the series of oscillation signals is taken at a sampling rate of least 180 samples/second, preferably 200-samples/heart cycle, and the digitised signals are stored in at least 9 bit resolution.

The method according to invention has a further advantageous characteristic, that the cuff is set to supra-systolic pressure range, over the systolic pressure, preferably by 35 millimetres of mercury, the Pulse Wave Velocity (PWV) value is calculated from the time shift of the main wave and the first reflected one using the distance between sternal notch and pubic bone measured on the patient, and/or the cuff (11) is set to the already determined diastolic pressure or near to this, the received heart cycle curve is divided into two parts with the ED end-point, and the Systolic Area Index (SAI) and Diastolic Area Index (DAI) values are established in this way.

BRIEF DESCRIPTION OF THE DRAWINGS

The invention is shown in detail by examples of embodiments in the attached figures without limitation, however, of either the applicability or the scope of claimed protection to the examples shown.

FIGS.

Figure 1:
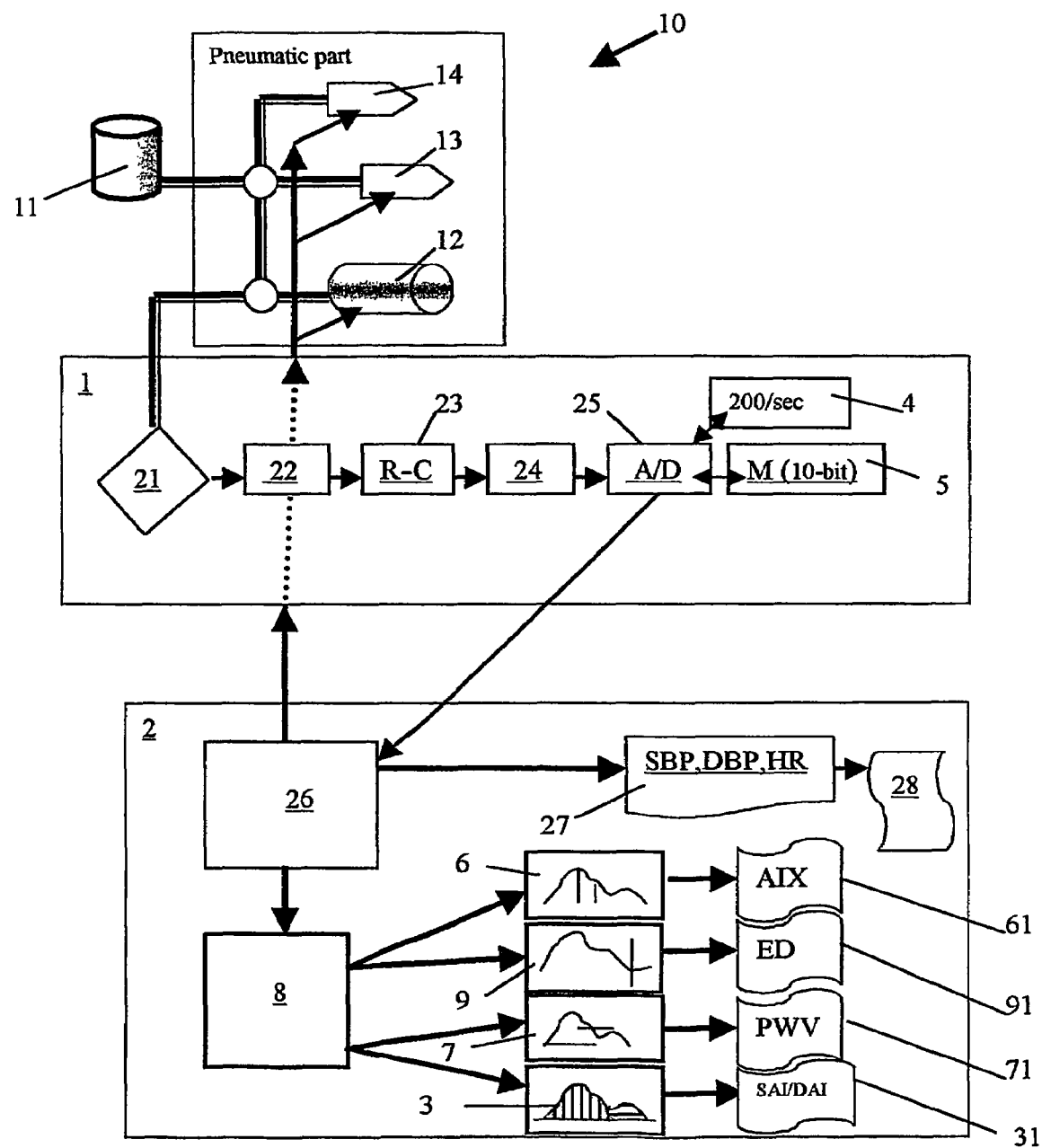

The FIG. 1 shows block diagram of the structure of the apparatus

Figure 2:
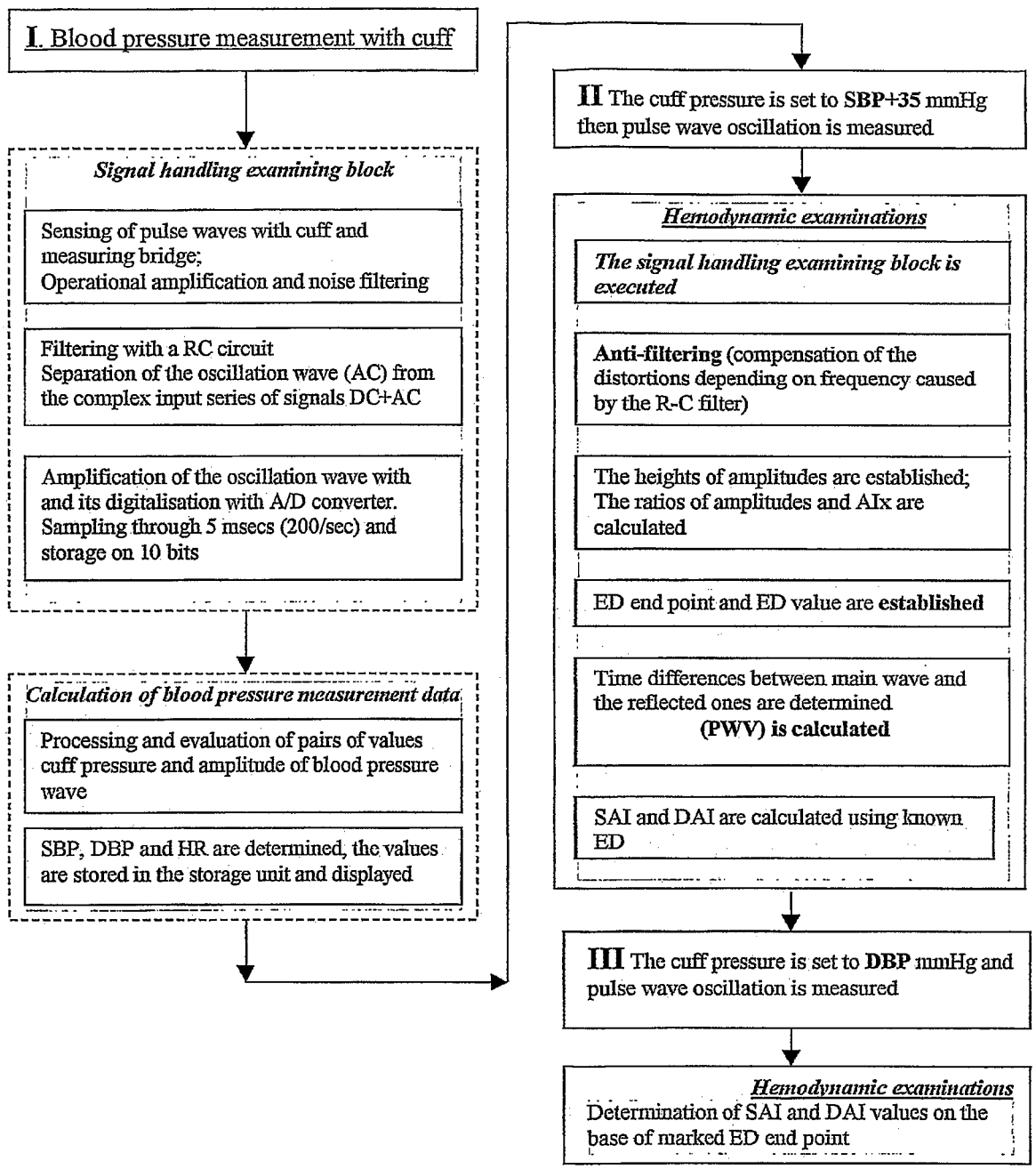

The FIG. 2 shows logical flowchart of effectuation of the method

Figure 3:
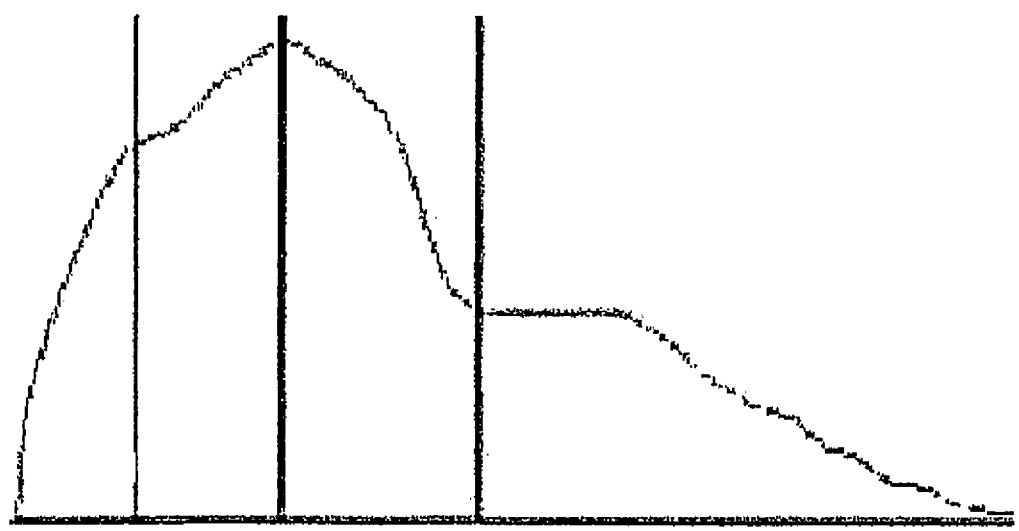

The FIG. 3 shows a characteristic oscillation curve of the heart cycle

Figure 4:
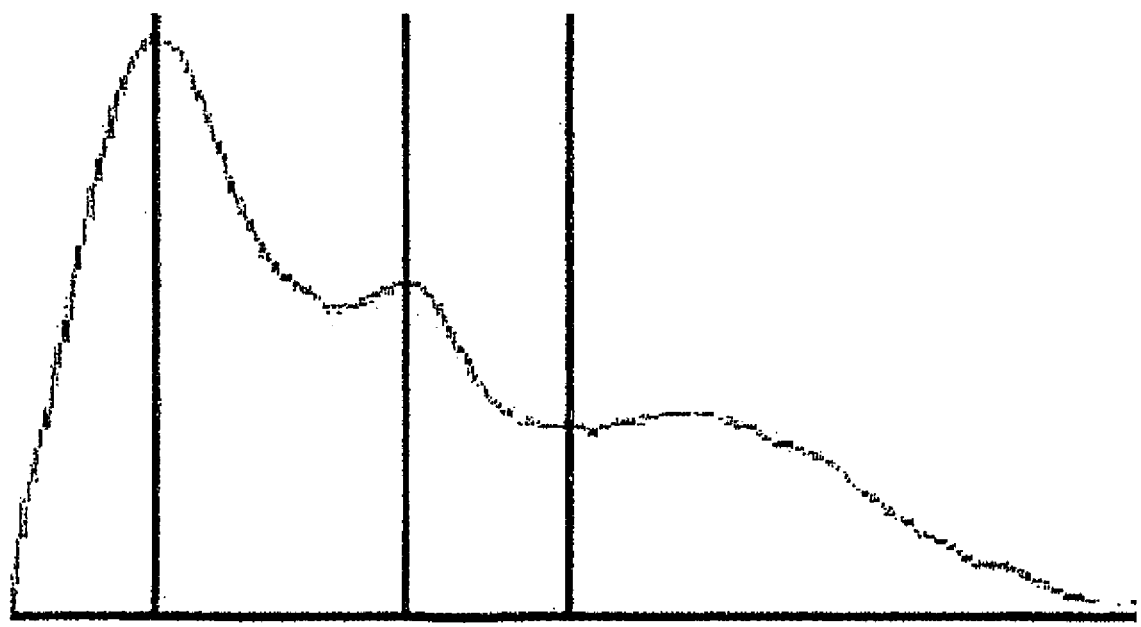

The FIG. 4 shows a further characteristic oscillation curve of the heart cycle

Figure 5:
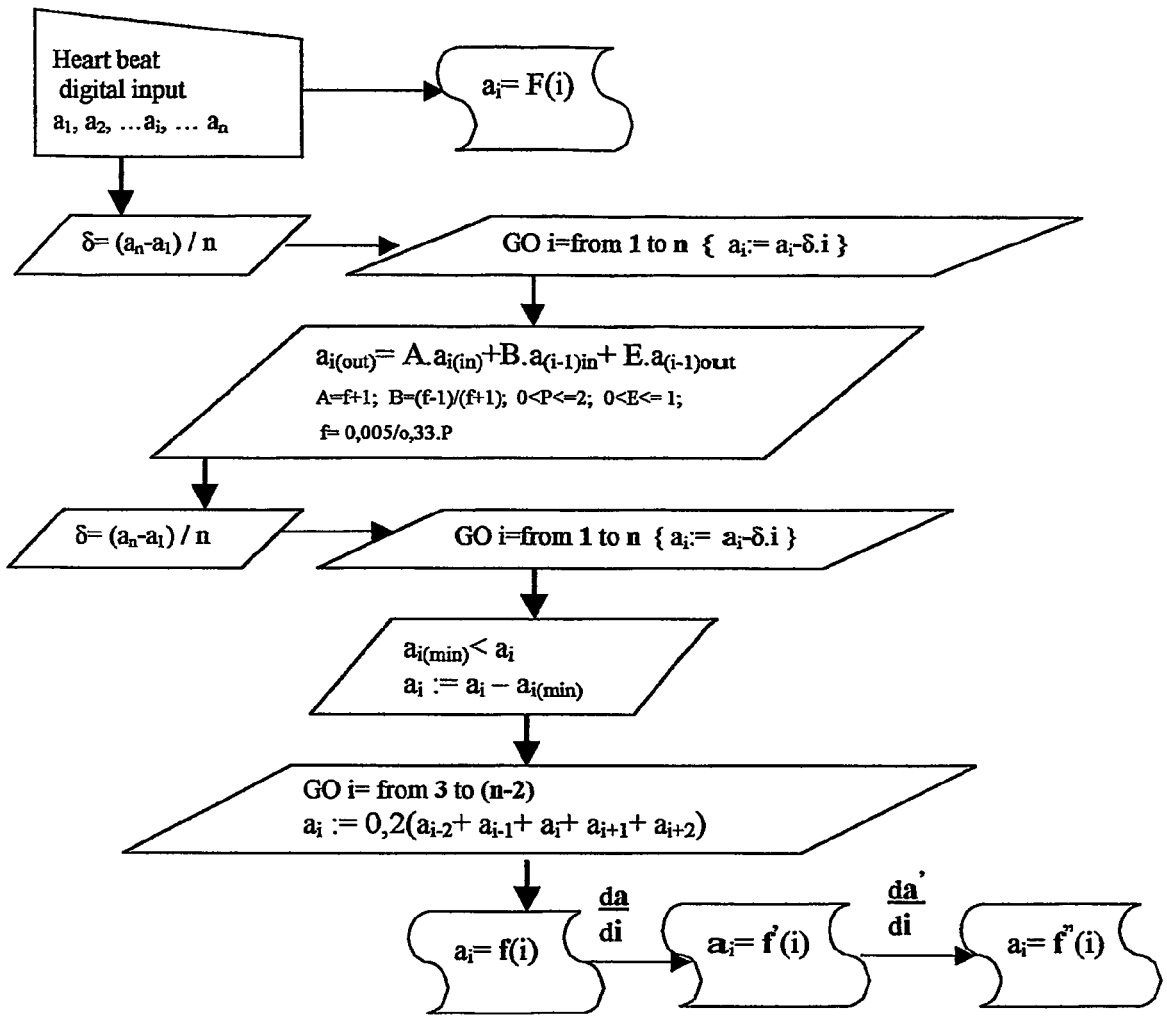

The FIG. 5 shows a simplified block diagram of the function flow of the "anti-filter".

Figure 6:
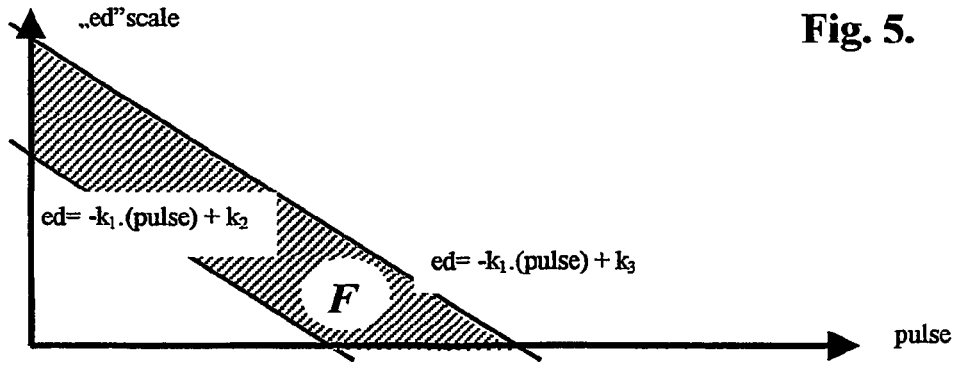

The FIG. 6 shows the diagram limiting the verification area of ED value

The FIG. 7 shows a simplified block diagram of the harmonised working of the amplitude arithmetic and time arithmetic units of the apparatus according to our invention.

DETAILED DESCRIPTION OF PREFERRED EMBODIMENTS

The structure of the apparatus 10 according to invention is partially the same as a traditional blood pressure meter but it differs from the traditional instrument in regard of the solutions of invention (see FIG. 1). It is well known that an automatic blood pressure meter consists of a pneumatic part and an electronic one. The pneumatic part consists of a pneumatic cuff 11 being the sensor at the same time a pump 12 a releasing valve 13 and an emergency valve 14. The cuff 11 put on the upper arm is applicable to constrict the arteria brachialis on the one hand and on the other hand it senses the pulse pressure wave of the artery and transmits as pressure change to a sensor 21 transforming it into electric resistance change like e. g. a piezoelectric crystal. Consequently the automatic blood pressure meter belongs to the non-invasive medical instruments. The sensor is the cuff 11 itself as opposed to the instruments using contact pressure sensors fastened on the patient's body above the artery. The pump 12 producing the internal pressure of the cuff 11 the controllable releasing valve 13 serving to diminish the pressure and the emergency valve 14 instantaneously terminating the constriction of the artery if the patient feels himself or herself sick belong to the pneumatic part of the blood pressure meter. The electronic part theoretically may be divided into two parts a signal detector 1 and an analyser 2. The signal detector converts the signal flow of pneumatic changes sensed by the cuff 11 into electric signal flow and treats them in such a way that data relating to blood pressure and suitable for evaluation are obtained. The analyser 2 processes and evaluates the signal flow duly amplified and cleared from disturbances. The Hungarian patent description of No. 220,528 describing one of such apparatuses may be mentioned as example. The analyser 2 controls the pneumatic system at the same time. The control is based on the fact whether the obtained and processed data are sufficient for the complete evaluation. The signal detector 1 is connected through the sensor 21 to the pneumatic part namely to the cuff 11. The sensor 21 is expediently connected into a bridge circuit so that the pulse pressure wave may be treated as electric voltage change in this way. A measuring amplifier 22 is connected to the sensor 21 to amplify the signal flow, to filter out the noise and to let through a defined desired frequency range. The output of the measuring amplifier 22 is connected to a filtering R-C element 23, which is connected to an A/D converter 25 through an amplifier 24. The filtering R-C element 23 is to select the oscillation signal flow i.e. the alternating component from the pulse wave analogue input signal. The amplifier 24 amplifies the oscillation signal flow so that the oscillation waves may be recognised, determined and their amplitudes are defined in the following operations. The A/D converter 25 converts the amplified oscillation signal flow into a digital signal flow. In the traditional blood pressure meters the pressure in the cuff 11 is stepwise diminished from a pressure above the supposed systolic one recording the pulse pressure belonging to each pressure step in the cuff 11. Consequently only one amplitude i.e. only the digitised values of the wave peaks should be recorded from the wave picture of each heart cycle. To accomplish this task it is sufficient to sample about 100 points per second from the analogue signal flow to find the wave peaks and the recording of samples of oscillation with resolution of 8 bits. The frequency of sampling and the resolution of signals do not allow in fact recognising particularities others than the maximal amplitude. The A/D converter 25 is provided with a sampler 4, which steers sampling of frequency at least twice higher than the traditional in the apparatus 10 according to our invention. The applied frequency of sampling is 200 per second in the example, corresponding generally to 200 samples per heart cycle The A/D converter 25 is equipped furthermore with a storage unit 5 of more than 8 bits in the example with one of 10 bits in the apparatus 10 according to our invention. We gained the experience showing that the oscillation signal flow in resolution of 10 bits can show unambiguously the fine structure in the oscillogram of a single heart cycle namely the main wave and the following reflected ones. It enables the successful application of the cuff 11 for measurement of hemodynamic characteristics on the base of the medical discovery described in the general description of the invention using the inventor's recognition based on the discovery. The program controller 26 arranged inside the analyser 2 puts into operation either the units for traditional blood pressure measurement in order to define and display the systolic blood pressure [SBP], the diastolic one [DBP] and the heart rate [HR], or those developed for determination and displaying the further hemodynamic characteristics. The blood pressure evaluation unit 27 determines the values of SBP, DBP and HR from the pairs of values of pressure in the cuff and pulse wave amplitude in compliance with the international medical practice, then either displays them through the blood pressure unit 28 connected to the evaluation unit 27 on the LCD of the apparatus 10 or prints them in defined form out.

When further hemodynamic characteristics should be defined, the A/D converter 25 and other units handling the signs are connected to the anti-filter 8 under command of the program controller 26. The anti-filter 8 compensates and amends all distortions using the inverse of the transmission function of the R-C filter 23, which appeared in the oscillation signal flow due to usage of the R-C filter 23 and the amplifier 24. Considering that the distortions originated in the filtering and amplification depend on the "frequency" of the oscillation signal flow or more particularly on the speed of signal change changing from point to point, the anti-filter 8 works in connection with this characteristic. The analyser 2 expediently connected to the anti-filter 8 comprises an amplitude arithmetic unit 6 a time arithmetic unit 7, a synthesising unit 9 and an integrating unit 3. The AIx output unit 61, the ED output unit 91, the PWV output unit 71, and the SAI/DAI output unit 31 is connected similarly to the blood pressure output unit 28. [The SAI means the Systole Area Index, the DAI means the Diastole Area Index. These are the areas under the heart cycle oscillation curvesector before and after the ED endpoint.] The amplitude arithmetic unit 6 determines the amplitudes of the main wave and the reflected waves and produces AIx and $AIx_{80}$ from them. The time arithmetic 7 determines the end points of the main wave and the first reflected one, calculating the value PWV from them using the distance between the artery carotis and artery femoralis of the patient. [The evaluation and the calculation of PWV may be done on the base of the time between starting point of the main wave and that of reflex waves (foot to foot) and/or the time between peaks of waves (peak to peak)] The synthesising unit 9 determines the end point of the ED, and the integrating unit 3 determines the SAI and DAI values on the base of ED endpoint, and their quotient being a characteristic information about the state of coronary perfusion of the heart. The analyser 2 chooses the representative heart cycle expediently from ten adjacently recorded heart cycles on the base of the most characteristic appearance of the wave peaks or in other cases the unit uses a virtual heart cycle being average of ten adjacent heart cycles.

The apparatus 10 according to invention may be also completed to Holter's apparatus for 24 hours' usage similarly to the traditional blood pressure meters. An advantageous embodiment of the apparatus is integrated with an automatic measuring and registering apparatus for 24 hours' usage in our example.

In another advantageous embodiment of the apparatus 10 according to invention the signal detector 1 and the processing analyser 2 may be expediently divided into a sampling basic apparatus and a professional evaluating one in a clinical (physician's) PC. The sampling of the blood pressure pulse wave with increased frequency and its storage with increased resolution has key importance even in this case.

An extraordinarily advantageous embodiment of the apparatus 10 according to invention is equipped with devices such as infrared eye or modem to telephone line or other I/O unit adequate to the applied telemetric system providing connection to a "home care" system. An important advantage of the apparatus according to invention is that the patient needing the measured data can put himself or herself the cuff 11 on and can start the measurement or enable a central telemetric controller to start it. There are a number of telemetric medicinal "home care" systems known in the specialised literature. One of them is the invention described in the Hungarian patent description of No. 222 052. The apparatus 10 according to invention connected to the "home care" system enhances highly advantageously the examining and supervising abilities of the system and the human biological information provided to physician.

Another embodiment and application of the apparatus 10 according to invention is the one equipped with blood pressure meter combined with ECG apparatus. A local anoxic status of the heart muscle (ischemia) is a prodrome and precedes the myocardial infarction with certain probability. The pathologic ECG status may be, however, successfully evaluated only in combination with data of blood pressure measurement. The known and widely used combined instrument automatically starts the blood pressure measurement if pathologic ECG status occurs. If the apparatus 10 is completed with the one according to invention more extensive hemodynamic data may be recognised in the critical episodes.

The method according to invention aims in addition to usual data of blood pressure measurement such as SBP, DBP, HR to getting knowledge of additional hemodynamic characteristics such as augmentation index (AIx), pulse wave velocity (PWV) and ejection duration (ED), and the above-mentioned SAI, DAI. The usage of the apparatus 10 and the work of their units is demonstrated below: (See the FIG. 2.)

The cuff 11 is put onto upper arm of the patient to the arteria brachialis. The following fact should be considered for the adequate performance of the measurement. The measurement with cuff provides specific opportunities and offers advantages among the non-invasive measurements if it is performed adequately. As opposed with the measurement with contact manometers pressed onto body surface to measure artery pressure the measurement with cuff does not depend on the skill of the examining person, the adequate pressure of sensor and the stability of pressure during measurement. It eliminates subjective errors and erroneous components originated therefrom. In the measurement with cuff the sensor is the cuff itself and the oscillation is tranismitted thereby from the pneumatic section to the electronic one. The cuff of reduced width to 66% of the one for measurement of adults wherein the hose goes round the arm is adequate for this purpose. Its width is 7 to 8 cm (children's size) but the perimeter is longer than usual.

The apparatus 10 performs the usual stepwise blood pressure measurement. The systolic blood pressure (SBP) and diastolic one (DBP) are recorded, and displayed or printed for the user. The pressure in the cuff is then increased above the measured SBP (into so-called supra systolic range) advantageously by 35 millimetres of mercury. An oscillation signal series of approximately ten continuous heart cycles is recorded, filtered and amplified by usual methods applied in usual automatic blood pressure measurement. The series of analogue signals is digitised with sampling frequency of 200 samples per second and the digitised values are stored and treated in resolution of 10 bits. The essence of the above-presented S+35 (above the systole by 35 millimetres of mercury) measurement is that the artery of upper arm is completely constricted, so no blood flow takes place during the measurement in this way. The oscillation of pressure, however, spreads in the blood in the blood vessels, as in liquid and it exerts pressure onto cuff 11. The measurement performed in the supra systolic range is based on the pressure waves and the disturbing effects of the blood flow are eliminated.

The cuff 11 should be adequately resilient in order to transmit immediately the pressure wave oscillation to the electronic section, which is reached by adequately high pressure in the cuff 11. The pressure should not be, however, too high, because it is uncomfortable and may be harmful to the person being examined on the one hand and it diminishes the sensibility of measurement on the other hand. The optimum of overpressure is about 35 millimetres of mercury according to our experience. We unified the consequent usage of 35 millimetres of mercury in order to ensure the reproducibility of measurements.

Figure 7A:
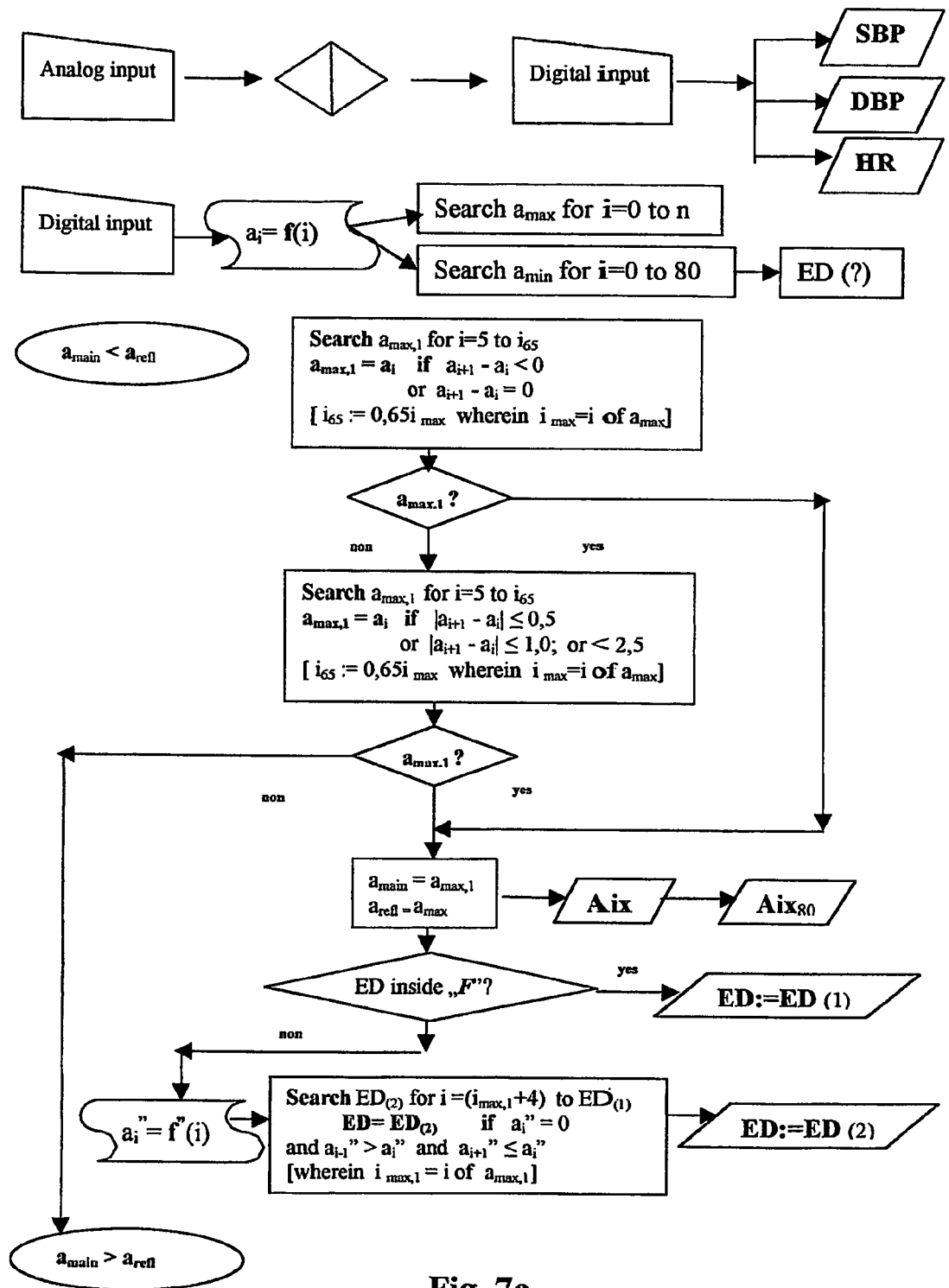
Figure 7B:
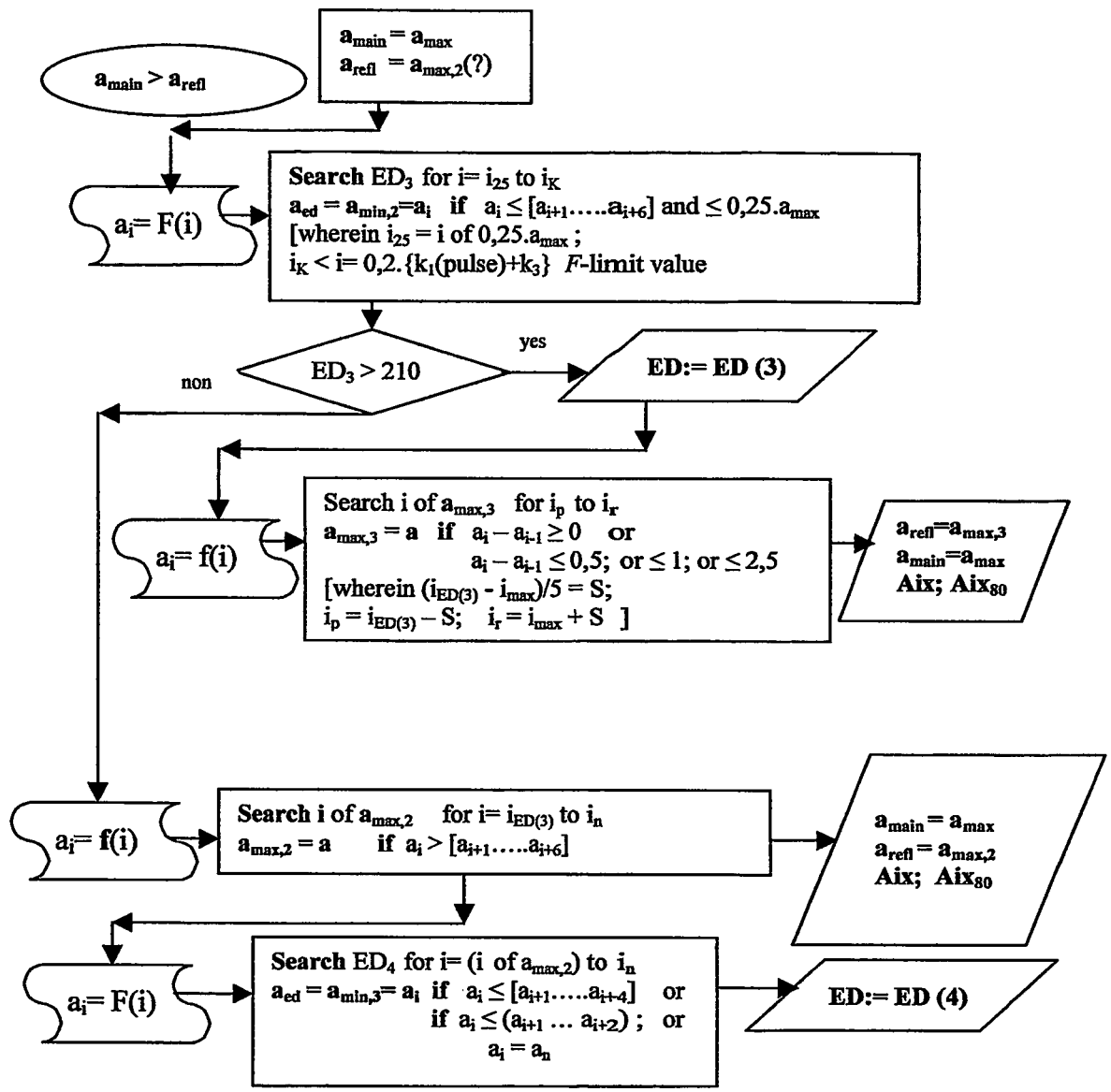

The working process of the analyser 2 is shown on the FIGS. 7a and 7b. The apparatus 10 takes a new sample after the traditional blood pressure measurement and submits the digitised series of signals to a correction using the anti-filter 8 to compensate the distortions caused by the previous RC filtering (see FIG. 5).

The anti-filtering enables to perform the method according to invention with resolution of 10 bits, which should be performed otherwise with transformation of much higher resolution. The elements required for higher resolution could raise the price of the apparatus 10. The original series of signals before anti-filtering $a_i = F(i)$ is stored in the storage in the storage unit 5. The corrected series of signals $a_i = f(i)$ and data series of its first and second derivatives $a'_i = f'(i)$ and $a''_i = f''(i)$ are also stored in the storage unit 5. In these series $a$ is the amplitude and $i$ its serial number on the time axis, where a time interval of 5 milliseconds is between every two i values in our example.

The average waveform accepted as representative is produced from the data flow of distortion-free heart cycles. The amplitudes of the main wave and the first reflected one give the AIx being characteristic for arteriosclerosis.

The real heart cycle curve may show a very wide variety. Two characteristic examples thereof are shown in the FIGS. 3 and 4. The main wave of heart cycle $[a_{main}]$ is smaller than the first reflected one $[a_{refl}]$ in the FIG. 3. A converse position is shown in the FIG. 4. It is shown in the FIGS. 7a and 7b how the amplitude arithmetic unit 6 and the synthesising unit 9 work together under control of the program controller 26. The places of maximum $[a_{max}]$ and minimum $[a_{min}]$ found in the corrected series of signals can theoretically determine the amplitude and place of the main wave, as well as the place of ED. The interpretation of the events depends, however, on, whether the analysed heart cycle curve belongs to the type of FIG. 3 or 4. We suppose the presence of a maximum smaller than $a_{max}$ before it. If the curve belongs to the type shown in the FIG. 3 AIx may be calculated from the two maximums and its value corrected to the heart rate is $$AIx_{80} = AIx + \{0.56 * (HR - 80)\}$$

according to the convention of the medical literature.

The place of the minimum is equal to ED, if it is within the zone F shown in the FIG. 6. (The values of $k_1$, $k_2$ and $k_3$ are determined by experience on the base of a great mass of measurements.) ED should be otherwise searched in the series of second derivatives [ED(2)]. If the curve belongs to the type shown in the FIG. 4 the program controller 26 starts the function shown in the FIG. 7b. The end point of ED should be searched in the series of uncorrected signals. If this point appears after 210 milliseconds, it should be accepted [ED(3)]. The reflected wave should be between [ED(3)] and $a_{max}$ in the corrected series of data in this case $[a_{max,3}]$. If the ED appears too short from medical viewpoint the reflected wave should be found after the minimum place $[a_{max,2}]$ followed by the real ED end point [ED(4)]. The apparatus determines AIx and ED on the base of main wave and reflected wave data proven as final and the time arithmetic unit calculates PWV using the distance between arteria carotis and arteria femoral given individually.

Having completed the measurement S+35, then the pressure of cuff 11 is set to the measured DBP or near to it and having put the ED end point found as described above onto axis $i$ of the digitised and corrected series of signals, the integrating unit 3 determines the area under the curve before the ED end point [SAI] and the one after that point [DAI] calculates their quotient then transmits them to the SAI/DAI output unit 31.

It is the significant difference between the supra-systolic measurement and the diastolic one that the arteria brachialis is completely closed i.e. there is no blood flow in the artery during the first measurement, consequently the artery diameter does not change. The blood's pressure in the artery prevails. The cuff seizes the changes of pressure. The blood flow is present at the measurement in the diastolic pressure range and the change of artery diameter takes place due to conveyance of the pulse wave. The cuff seizes this change in this case.

All hemodynamic characteristics are determined in the more reliable pressure range S+35 as result of usage of our apparatus and method according to invention, as it is unnecessary to transmit the values measured at systole to diastole to complete successfully the measurement.

In summary the apparatus and method according to invention offer a new technical solution for accomplishment of an already introduced and accepted method of medical diagnostics. The solution originates from a new medical discovery of the inventors and the essence of the invention is a practical technical embodiment of the discovery. The invention is new, because no reliable and accurate transformation of the hemodynamic processes in the central aorta was known before using non-invasive occlusive method and apparatus i. e. using the cuff for blood pressure measurement as sensor. There has not been known any method and apparatus up to now, which the said hemodynamic characteristics reliably transforms using a cuff as sensor and provides data in a form suitable for further evaluation.

The solution according to invention provides an inexpensive easy to use method and apparatus, which may be introduced widely and quickly. They do not require expensive personal, as the patient himself or herself can use the apparatus alone.

The invention claimed is:

1. Apparatus An apparatus for measuring hemodynamic parameters, by non-invasive, cuff based occlusive, blood pressure measurement, which apparatus comprises occlusive, oscillometric automatic blood pressure meter and units, determining the values of hemodynamic parameters, comprising
    an oscillation wave separating and storing signal detector for detecting an oscillation signal, the sampling rate thereof is at least 200/heart cycle; and said signal detector has a storage unit resolution that is organized at least 9 bit,
    a digital anti-filter connected to the signal detector to compensate the distortions rising at sampling, separating and digitizing the oscillation wave, detected by the signal detector,
    an amplitude arithmetic unit connected to the anti-filter establishing an Augmentation Index (Aix); and
    a synthesizing unit connected to the anti-filter establishing an Ejection Duration (ED).

2. The apparatus according to claim 1, wherein the sampling rate of the signal detector is 180-220/second.

3. The apparatus according to claim 1, wherein the storage unit storing the signals, generated by the oscillation wave, is organized 10-12 bit.

4. The apparatus according to claim 1 further comprising a time-arithmetic unit establishing a Pulse Wave Velocity (PWV), or integrator unit establishing a Systole Area Index (SAI) and Diastole Area Index (DAI).

5. The apparatus according to claim 1, wherein the amplitude arithmetic unit, the synthesizing unit, a time-arithmetic unit, or an integrator unit are joined to a common program controller, and compiled to an analyzer.

6. The apparatus according to claim 1, further comprising a portable, 24 h ambulatory blood pressure monitor.

7. The apparatus according to claim 1, further comprising a telemedical home care system.

8. The apparatus according to claim 1, further comprising a 24 h blood pressure monitor, which is controlled by a built-in ECG.

9. A method for non-invasive measurement of hemodynamic characteristics comprising the steps of:
- (a) performing a standard stepwise blood pressure measurement using an occlusive, pressure-sensor cuff placed on the brachial artery;
- (b) storing systolic blood pressure (SBP), diastolic blood pressure (DBP), and heart rate (HR) values;
- (c) subsequently setting the cuff to supra-systolic pressure range over the systolic pressure;
- (d) performing a pressure oscillometric pulse wave detection at supra-systolic pressure range, receiving oscillation curve and simultaneously by an "anti-filter" process compensating for signal distortions appearing at sampling;
- (e) calculating an Augmentation Index (Aix) on the basis of the wave amplitudes from the oscillation curves so received; and
- (f) calculating the Ejection Duration (ED) value on the oscillating curve determining the minimum point after the first reflex wave.

10. The method according to claim 9, wherein the sampling rate of the pressure oscillometric rules wave detection is taken at least 180 samples per second, and the digitized signals of the oscillation curve are stored at least in 9 bit resolution.

11. The method according to claim 9, wherein the cuff is set to +35 mmHG pressure, over the systolic pressure, a pulse wave velocity (PMV) value is calculated from a time shift of the main wave and the first reflex, respectively of a measured sternal notch and pubic bone distance of a patient, or the cuff is set at or near to a previously determined diastolic value, and the received heart cycle curve is divided into two parts with the ED end-point, to constitute Systole Area Index (SAI) and Diastole Area Index (DAI) values.

* * * * *

UNITED STATES PATENT AND TRADEMARK OFFICE
CERTIFICATE OF CORRECTION

PATENT NO.        : 7,468,037 B2
APPLICATION NO. : 10/596240
DATED             : December 23, 2008
INVENTOR(S)       : Illyes et al.

It is certified that error appears in the above-identified patent and that said Letters Patent is hereby corrected as shown below:

Column 12, line 11, (Line 2 of Claim 10) after the word "oscillometric", please change "rules" to correctly read:   --pulse--.

Signed and Sealed this

Twenty-fourth Day of March, 2009

JOHN DOLL
*Acting Director of the United States Patent and Trademark Office*